(12) United States Patent
Lu

(10) Patent No.: US 8,785,472 B2
(45) Date of Patent: Jul. 22, 2014

(54) USE OF DEXTROMETHORPHAN IN TREATING ADDICTIVE BEHAVIOR OR BIPOLAR DISORDER

(75) Inventor: Ru-Band Lu, Tainan (TW)

(73) Assignee: National Cheng Kung University, Tainan (TW)

(*) Notice: Subject to any disclaimer, the term of this patent is extended or adjusted under 35 U.S.C. 154(b) by 390 days.

(21) Appl. No.: 12/857,956

(22) Filed: Aug. 17, 2010

(65) Prior Publication Data

US 2011/0281904 A1    Nov. 17, 2011

Related U.S. Application Data

(60) Provisional application No. 61/333,305, filed on May 11, 2010.

(51) Int. Cl.
*A61K 31/44* (2006.01)
*A61K 31/485* (2006.01)

(52) U.S. Cl.
CPC .................................. *A61K 31/485* (2013.01)
USPC ........................................................ 514/289

(58) Field of Classification Search
CPC .................................................... A61K 31/485
USPC ........................................................ 514/289
See application file for complete search history.

(56) References Cited

U.S. PATENT DOCUMENTS

2006/0167032 A1* 7/2006 Galer et al. ............ 514/282

FOREIGN PATENT DOCUMENTS

DE    102007009888    * 9/2008 ............ A61K 31/122

OTHER PUBLICATIONS

Akerele E, Bisaga A, Sullivan MA, Garawi F, Comer SD, Thomas AA, Nunes EV, Kleber HD. Dextromethorphan and quinidine combination for heroin detoxification. Am J Addict. May-Jun. 2008;17(3):176-80.*
Banken JA, Foster H. Dextromethorphan. Ann N Y Acad Sci. Oct. 2008;1139:402-11.*
Bisaga A, Gianelli P, Popik P. Opiate withdrawal with dextromethorphan. Am J Psychiatry. Apr. 1997;154(4):584.*
Soczynska JK, Kennedy SH, Goldstein BI, Lachowski A, Woldeyohannes HO, McIntyre RS. The effect of tumor necrosis factor antagonists on mood and mental health-associated quality of life: novel hypothesis-driven treatments for bipolar depression?*
Kukanich B1, Papich MG. Plasma profile and pharmacokinetics of dextromethorphan after intravenous and oral administration in healthy dogs. J Vet Pharmacol Ther. Oct. 2004;27(5):337-41.*
Soczynska JK1, Kennedy SH, Goldstein BI, Lachowski A, Woldeyohannes HO, McIntyre RS. The effect of tumor necrosis factor antagonists on mood and mental health-associated quality of life: novel hypothesis-driven treatments for bipolar depression? Neurotoxicology. Jul. 2009;30(4):497-521. Epub Mar. 24, 2009.*
Joan Ellen Zweben et al., Methadone Maintenance in the Treatment of Opioid Dependence, The Western Journal of Medicine, May 1990, pp. 588-599, vol. 152, Issue 5.
Barbara Broers et al., Inpatient Opiate Detoxification in Geneva: Follow-Up at 1 and 6 Months, Drug and Alcohol Dependence, 2000, p. 85-92, vol. 58.
Michael Gossop, Lapse, Relapse and Survival Among Opiate Addicts after Treatment, British Journal of Psychiatry, 1989, pp. 348-353, vol. 154.
Adam Bisaga et al., In Search of a New Pharmacological Treatment for Drug and Alcohol Addiction: N-methyl-D-aspartate (NMDA) Antagonists, Drug and Alcohol Dependence, 2000, pp. 1-15, vol. 59.
Barbara H. Herman et al., Clinical Medications Development for Opiate Addiction: Focus on Nonopioids and Opioid Antagonists for the Amelioration of Opiate Withdrawal Symptoms and Relapse Prevention, Seminars in Neuroscience, 1997, pp. 158-172, vol. 9.
James W. Cornish et al., A Randomized, Double-Blind, Placebo-Controlled Safety Study of High-Dose Dextromethorphan in Methadone-Maintained Male Inpatients, Drug and Alcohol Dependence, 2002, pp. 177-183, vol. 67.
L. J. Bristow et al., Competitive and Glycine/NMDA Receptor Antagonists Attenuate Withdrawal-induced Behaviours and Increased Hippocampal Acetylcholine Efflux in Morphine-dependent Rats, Neuropharmacology, 1997, pp. 241-250, vol. 36, No. 2.
Piotr Popik et al., Inhibition of Reinforcing Effects of Morphine and Motivational Aspects of Naloxone-Precipitated Opioid Withdrawal by N-Methyl-D-Aspartate Receptor Antagonist, Memantine, The Journal of Pharmacology and Experimental Therapeutics, 1997, pp. 854-865, vol. 280, No. 2, U.S.A.
P. Popik et al., Inhibition of Reinforcing Effects of Morphine and Naloxone-Precipitated Opioid Withdrawal by Novel Glycine Site and Uncompetitive NMDA Receptor Antagonists, Neuropharmacology, 1998, pp. 1033-1042, vol. 37.
Esperanza Del Pozo et al., The NMDA Receptor Antagonist Dizocilpine (MK-801) Stereoselectively Inhibits Morphine-Induced Place Preference Conditioning in Mice, Pyschopharmacology, 1996, pp. 209-213, vol. 125.
Hack-Seang Kim et al., Inhibition by MK-801 of Morphine-Induced Conditioned Place Preference and Postsynaptic Dopamine Receptor Supersensitivity in Mice, Pharmacology Biochemistry & Behavior, 1996, pp. 11-17, vol. 55, No. 1, U.S.A.
Lawrence W. Fitzgerald et al., Drugs of Abuse and Stress Increase the Expression of GluR1 and NMDAR1 Glutamate Receptor Subunits in the Rat Ventral Tegmental Area: Common Adaptations among Cross-Sensitizing Agents, The Journal of Neuroscience, Jan. 1, 1996, pp. 274-282, vol. 16, No. 1.

(Continued)

*Primary Examiner* — Paul Zarek
(74) *Attorney, Agent, or Firm* — Hannah M. Tien

(57) ABSTRACT

The present invention provides a method for treating addictive behavior, comprising administering Dextromethorphan (DM) to a subject suffering addictive behavior. The present invention also provides a method for treating bipolar disorder, comprising administering Dextromethorphan (DM) to a subject suffering bipolar disorder.

11 Claims, 11 Drawing Sheets

(56) References Cited

OTHER PUBLICATIONS

Charles E. Inturrisi, Preclinical Evidence for a Role of Glutamatergic Systems in Opioid Tolerance and Dependence, Seminars in Neuroscience, 1997, pp. 110-119, vol. 9.

Guorong Li et al., Protective effect of dextromethorphan against endotoxic shock in mice, Biochemical Pharmacology, 2005, 233-240, vol. 69.

Yuxin Liu et al., Dextromethorphan Protects Dopaminergic Neurons against Inflammation-Mediated Degeneration through Inhibition of Microglial Activation, The Journal of Pharmacology and Experimental Therapeutics, 2003, pp. 212-218, vol. 305, No. 1, U.S.A.

Wei Zhang et al., Neuroprotective effect of dextromethorphan in the MPTP Parkinson's disease model: role of NADPH oxidase, The FASEB Journal, Jan. 20, 2004.

Wei Zhang et al., 3-Hydroxymorphinan is neurotrophic to dopaminergic neurons and is also neuroprotective against LPS-induced neurotoxicity, The FASEB Journal, Dec. 13, 2004.

John J. Madden et al., Opiate binding sites in the cellular immune system: expression and regulation, Journal of Neuroimmunology, 1998, pp. 57-62, vol. 83.

Bruce A. Fuchs et al., Morphine Induces Apoptosis in Murine Thymocytes in Vivo but not in Vitro: Involvement of Both Opiate and Glucocorticoid Receptors, The Journal of Pharmacology and Experimental Therapeutics, 1993, pp. 417-423, vol. 266, No. 1, USA.

Yoshitatsu Sei et al., Morphine-Induced Thymic Hypoplasia Is Glucocorticoid-Dependent, The Journal of Immunology, Jan. 1, 1991, pp. 194-198, vol. 146, No. 1, USA.

David O. Freier et al., A Mechanism of Action for Morphine-Induced Immunosuppression : Corticosterone Mediates Morphine-Induced Suppression of Natural Killer Cell Activity, The Journal of Pharmacology and Experimental Therapeutics, 1994, pp. 1127-1133, vol. 270, No. 3, USA.

R. Daniel Mellon et al., Role of central opioid receptor subtypes in morphine-induced alterations in peripheral lymphocyte activity, Brain Research, 1998, pp. 56-67, vol. 789.

Geng-Chang Yeh et al., Analysis of Pharmacokinetic Parameters for Assessment of Dextromethorphan Metabolic Phenotypes, Journal of Biomedical Science, 2003, pp. 552-564, vol. 10.

Hea Won Kim et al., Alexithymia and Stress Response Patterns among Patients with Depressive Disorders in Korea, Psychiatry Invest, 2009, pp. 13-18, vol. 6.

Sinead M. O'Brien et al., Cytokine profiles in bipolar affective disorder: Focus on acutely ill patients, Journal of Affective Disorders, 2006, pp. 263-267, vol. 90.

Elisa Brietzke et al., Comparison of cytokine levels in depressed, manic and euthymic patients with bipolar disorder, Journal of Affective Disorders, 2009, pp. 214-217, vol. 116.

Jagadeesh S. Rao et al., Increased excitotoxicity and neuroinflammatory markers in postmortem frontal cortex from bipolar disorder patients, Mol Psychiatry, Apr. 2010, pp. 384-392, vol. 15, No. 4.

Julien Mendlewicz et al., Shortened onset of action of antidepressants in major depression using acetylsalicylic acid augmentation: a pilot open-label study, International Clinical Psychopharmacology, 2006, pp. 227-231, vol. 21.

P-S Chen et al., Valproate protects dopaminergic neurons in midbrain neuron/glia cultures by stimulating the release of neurotrophic factors from astrocytes, Molecular Psychiatry, 2006, pp. 1116-1125, vol. 11.

Scott L. Zeger et al., Markov Regression Models for Time Series: A Quasi-Likelihood Approach, Biometrics, Dec. 1988, p. 1019-1031, vol. 44, No. 4.

Katerina Dvorakova et al., Increased Expression and Secretion of Interleukin-6 in Patients with Barrett's Esophagus, Clinical Cancer Research, Mar. 15, 2004, pp. 2020-2028, vol. 10.

\* cited by examiner

USE OF DEXTROMETHORPHAN IN TREATING ADDICTIVE BEHAVIOR OR BIPOLAR DISORDER

BACKGROUND OF THE INVENTION

Opioid dependence is a severe public health problem (Zweben J E, Payte J T. (1990) Methadone maintenance in the treatment of opioid dependence. A current perspective. Western Journal of Medicine. 152(5):588-99). Current efforts to taper individuals off opioid medications often lead to limited results due to a high relapse rate (Broers B, Gilner F, Dumont P, Mino A. (2000) Inpatient opiate detoxification in Geneva: follow-up at 1 and 6 months. Drug Alcohol Depend. 58: 85-92; Gossop M, Green L, Phillips G, Bradley B. (1989) Lapse, relapse and survival among opiate addicts after treatment. A prospective follow-up study. Br. J. Psychiatry. 154: 348-353) and troublesome subjective symptoms. Although substitution therapies with methadone for opioid dependence have been found to be effective, the relapse rates following discontinuation of methadone remain high, suggesting that substituting therapies might not be sufficient in the treatment of opioid dependence and addictive diseases (Bisaga A, Popik P. (2000) In search of a new pharmacological treatment for drug and alcohol addiction: N-methyl-D-aspartate (NMDA) antagonists. Drug Alcohol Depend. 59: 1-15).

Dextromethorphan (DM) is an effective and widely used antitussive drug. It is a dextrorotatory opioid derivative that does not act on opioid receptors but is a noncompetitive N-methyl-D-aspartate (NMDA) receptor antagonist. DM may be useful in the treatment of opioid dependence, particularly as a means of reducing tolerance to methadone during replacement therapy. In animal models, NMDA antagonists modulate many effects of chronic administration of opioids. NMDA antagonists alleviate physical withdrawal syndrome, attenuate ongoing drug dependence, reduce the tolerance of opioid, and inhibit the reward dependence (Bisaga A, Popik P. (2000) In search of a new pharmacological treatment for drug and alcohol addiction: N-methyl-D-aspartate (NMDA) antagonists. Drug Alcohol Depend. 59: 1-15). Several studies have indicated that NMDA receptor antagonists reduce the development of tolerance to the analgesic effects of opiates (Herman B H, O'Brien C P. (1997) Clinical medication development for opiate addiction: focus on nonopioids and opioid antagonists for the amelioration of opiate withdrawal symptoms and relapse prevention. Semin. Neurosci. 9: 158-172). Furthermore, by reducing the development of opioid tolerance, NMDA receptor antagonists could be particularly useful in methadone maintenance therapy because patients could be maintained at lower dosages, leading to fewer withdrawal symptoms when methadone therapy is terminated (Cornish J W et al. (2002) A randomized, double-blind, placebo-controlled safety study of high-dose dextromethorphan in methadone-maintained male inpatients. Drug & Alcohol Dependence. 67(2): 177-83).

NMDA receptor antagonists reduce the physical aspects of the expression of morphine dependence as measured by naloxone-precipitated withdrawal (Bristow L J, Hogg J E, Hutson P H. (1997) Competitive and glycine: NMDA receptor antagonists attenuate withdrawal-induced behaviours and increased hippocampal acetylcholine efflux in morphine-dependent rats. Neuropharmacology. 36: 241-250; Popik P, Danysz W. (1997) Inhibition of reinforcing effects of morphine and motivational aspects of naloxone-precipitated opioid withdrawal by N-methyl-D-aspartate receptor antagonist, memantine. J. Pharmacol. Exp. Ther. 280: 854-865; Popik P, Mamczarz J, Fraczek M, Widla G, Hesselink M, Danysz W. (1998) Inhibition of reinforcing effects of morphine and naloxone-precipitated opioid withdrawal by novel glycine site and uncompetitive NMDA receptor antagonists. Neuropharmacology. 37: 1033-1042) and may attenuate not only the physical but also affective and motivational components of abstinence states, as well as craving (Cornish J W et al. (2002) A randomized, double-blind, placebo-controlled safety study of high-dose dextromethorphan in methadone-maintained male inpatients. Drug & Alcohol Dependence. 67(2): 177-83). By reducing withdrawal symptoms, such medications should be beneficial for the patients during the acute detoxification phase of treatment for opioid dependence (Cornish J W et al. (2002) A randomized, double-blind, placebo-controlled safety study of high-dose dextromethorphan in methadone-maintained male inpatients. Drug & Alcohol Dependence. 67(2): 177-83).

NMDA antagonists have been shown in mice to inhibit morphine self-administration and to inhibit both the development and expression of morphine conditioned place preference (Popik P, Mamczarz J, Fraczek M, Widla G, Hesselink M, Danysz W. (1998) Inhibition of reinforcing effects of morphine and naloxone-precipitated opioid withdrawal by novel glycine site and uncompetitive NMDA receptor antagonists. Neuropharmacology. 37: 1033-1042; Del Pozo E, Barrios M, Baeyens J M. (1996) The NMDA receptor antagonist dizocilpine (MK-801) stereoselectively inhibits morphine-induced place preference conditioning in mice. Psychopharmacology. 125: 209-213; Kim H, Jang C, Park W. (1996) Inhibition by MK-801 of morphine induced conditioned place preference and postsynaptic dopamine receptor supersensitivity in mice. Pharmacol. Biochem. Behav. 55: 11-17). These results suggest that DM could have clinical utilities in preventing the development and expression of conditioned drug-dependence effects in humans.

Chronic exposure to morphine results in a number of biochemical adaptations of the glutamatergic receptor system in the limbic system (Fitzgerald L W, Ortiz J, Hamedani A G, Nestler E J. (1996) Drugs of abuse and stress increase the expression of GluR1 and NMDAR1 glutamate receptor subunits in the rat ventral tegmental area: common adaptations among cross-sensitizing agents. J. Neurosci. 16: 274-282). Excitatory amino acids are involved in the mediation of many neurochemical and behavioral effects resulting from chronic exposure to abusing drugs, some of which can be prevented or reversed using glutamatergic antagonists (Inturrisi C E. (1997) Preclinical evidence for a role of glutamatergic systems in opioid tolerance and dependece. Semin. Neurosci. 9: 110-119). Furthermore, the continued self-administration of abusive drugs, including opioid, may result in an overstimulation of dopamine in the brain reward centers and an increased release of excitatory amino acids (including glutamate), leading to the development of tolerance and dependence which could be blocked by glutamate antagonists (Herman B H, O'Brien C P. (1997) Clinical medication development for opiate addiction: focus on nonopioids and opioid antagonists for the amelioration of opiate withdrawal symptoms and relapse prevention. Semin. Neurosci. 9: 158-172).

In addition to the above-mentioned NMDA blocking effects, DM has been reported to afford neuroprotection on dopamine neurons in several inflammation-based animal Parkinson's disease models (Li G, Liu Y, Tzeng N S, Cui G, Block M L, Wilson B, Qin L, Wang T, Liu B, Liu J, Hong J S. (2005) Protective effect of dextromethorphan against endotoxic shock in mice. Biochemical Pharmacology. 69(2): 233-40; Liu Y, Qin L, Li G, Zhang W, An L, Liu B, Hong J S. (2003) Dextromethorphan protects dopaminergic neurons against inflammation-mediated degeneration through inhibition of microglial activation. Journal of Pharmacology & Experimental Therapeutics. 305(1):212-8; Zhang W, Wang T, Qin L, Gao H M, Wilson B, Ali S F, Zhang W, Hong J S, Liu B. (2004) Neuroprotective effect of dextromethorphan in the MPTP Parkinson's disease model: role of NADPH oxidase. FASEB Journal. 18(3): 589-91; Zhang W, Qin L, Wang T, Wei S J, Gao H M, Liu J, Wilson B, Liu B, Zhang W, Kim H C, Hong J S. (2005) 3-hydroxymorphinan is neurotrophic to dopaminergic neurons and is also neuroprotective against LPS-induced neurotoxicity. FASEB Journal. 19(3): 395-7). Zhang et al. (2004) obtained novel findings that 1-10 µM DM protected dopamine neurons against lipo-polysaccharide (LPS)-induced reduction of dopamine uptake in rat primary mixed mesencephalic neuron-glia cultures. Morphologically, in LPS-treated cultures, besides the reduction of an abundance of dopamine neurons, the dendrites of the remaining dopamine neurons were significantly less elaborative than those in the controls. In cultures pretreated with DM (10 µM) before LPS stimulation, dopamine neurons were significantly more numerous and the dendrites less affected. Significant neuroprotection was observed in cultures with DM added up to 60 minutes after the addition of LPS. Thus, DM significantly protects monoamine neurons not only with pretreatment but also with post-treatment (Zhang W, Wang T, Qin L, Gao H M, Wilson B, Ali S F, Zhang W, Hong J S, Liu B. (2004) Neuroprotective effect of dextromethorphan in the MPTP Parkinson's disease model: role of NADPH oxidase. FASEB Journal. 18(3): 589-91). Animal studies using both LPS and MPTP PD models also show potent protective effect of DM (Zhang W, Wang T, Qin L, Gao H M, Wilson B, Ali S F, Zhang W, Hong J S, Liu B. (2004) Neuroprotective effect of dextromethorphan in the MPTP Parkinson's disease model: role of NADPH oxidase. FASEB Journal. 18(3): 589-91).

The mechanism of the neuronprotective effect of DM is associated with the inhibition of microglia over-activation by inhibition of superoxide anion production from NADPH-oxidase, and this neuroprotective effect of DM is not associated with its NMDA receptor antagonist property. Zhang et al. (2005) examined several NMDA receptor antagonists, including MK801, AP5 and memantine. They found no correlation between the affinity of NMDA receptor antagonist activity and potency of the neuroprotective effect on dopamine neurons. On the contrary, a better correlation was observed between the anti-inflammatory potency and neuronprotection. These results suggest that the dopamine neuroprotection provided by DM in the inflammation-related neurodegenerative models is not mediated through the NMDA receptor. This conclusion is not in conflict with previous reports, indicating that NMDA receptor blockade is associated with the neuroprotective effects of DM in the acute glutamate-induced excitotoxicity models.

Opioid agonists have been reported to modulate the immune system through opioid receptors in the central nervous system (CNS). Direct actions of opiates on immune cells were observed in in vitro studies (Madden, J. J., W. L. Whaley, et al. (1998). Opiate binding sites in the cellular immune system: expression and regulation. J Neuroimmunol 83(1-2): 57-62). Opioid receptors, including µ3 and δ isoforms, were found in immune cells. Indirect actions of morphine also can be demonstrated in the immunological system. Morphine induces thymocyte apoptosis in vivo but not in vitro (Fuchs, B. A. and S. B. Pruett (1993). Morphine induces apoptosis in murine thymocytes in vivo but not in vitro: involvement of both opiate and glucocorticoid receptors. J Pharmacol Exp Ther 266(1): 417-23). Thymus hypoplasia was shown to be glucocorticoid (GC)-dependent (Sei, Y., K. Yoshimoto, et al. (1991). "Morphine-induced thymic hypoplasia is glucocorticoid-dependent." J Immunol 146(1): 194-8). GC-dependent effects of morphine activate the hypothalamic-pituitary-adrenal (HPA) axis. The activation of the HPA axis increases the products of GC as potent immunomodulatory hormones (Freier, D. O. and B. A. Fuchs (1994). A mechanism of action for morphine-induced immunosuppression: corticosterone mediates morphine-induced suppression of natural killer cell activity. J Pharmacol Exp Ther 270(3): 1127-33; Mellon, R. D. and B. M. Bayer (1998). Role of central opioid receptor subtypes in morphine-induced alterations in peripheral lymphocyte activity. Brain Res 789(1): 56-67).

Based on the above-mentioned evidence, the Applicant hypothesize that DM add-on therapy to long-action methadone maintained treatment method for opioid dependence instead of opioid use. The optimal dose of DM for this kind of usage is not clear. Bisaga et al. reported the dosage of 375 mg/day DM for heroin addicts undergoing withdrawal. In Cornich's study, participants received doses of 120, 240, and 480 mg/day of DM in increasing order. DM at high doses caused mild elevations of heart rate, blood pressure, temperature, and plasma bromide (Cornish J W et al. (2002) A randomized, double-blind, placebo-controlled safety study of high-dose dextromethorphan in methadone-maintained male inpatients. Drug & Alcohol Dependence. 67(2): 177-83). Particularly among Hang Chinese in Taiwan, DM has been reported to have quite different dextromethorphan metabolic enzyme P450 2D6 from that of Western population (Yeh G C, Tao P L, Ho H O, Lee Y J, Chen J Y, Sheu M T. (2003) Analysis of pharmacokinetic parameters for assessment of dextromethorphan metabolic phenotypes. J. Biomed. Sci. 10: 552-564).

Bipolar disorder (BP), characterized by a dysregulation of mood, impulsivity, risky behavior and interpersonal problems, is a recurrent and often chronic psychiatric illness. According to World Health Organization (WHO), it is associated with functional impairment, elevated suicide rates and utilization of mental health systems. Two subtypes of bipolar disorder, including bipolar I (BP-I) and bipolar II (BP-II) have been emphasized (American Psychiatric Association, 2000). However, bipolar disorder is commonly under-recognized even in psychiatric settings, especially bipolar-II subtype. As many as 40% of patients with bipolar disorders are initially misdiagnosed, and it may take years before those patients receive correct diagnosis and appropriate treatment. The missed treatment likely plays a part in increasing risk for suicide, mania and chronic psychosocial suffering, adding further to the burden on both patients and society. Even when the patients receive correctly diagnosed, fewer than 50% patients are treated successfully (NIMH 2002), and 10-15% may eventually die as a result of suicide.

While the pharmacological guidelines for treatment are well established, treatment for bipolar disorder remains less than ideal. Most individuals still have breakthrough episodes or significant residual symptoms while on medication (NIMH 2002). In addition, functional deficits often remain even when patients are in remission (NIMH 2002). Because many patients with bipolar disorder remain symptomatic, even while fully adherent to their medication regimens, the need for greater understanding of the pathogenesis of this illness from the research on the pharmacological mechanisms of bipolar medications is all the more urgent. The major medication therapy of bipolar disorders is mood stabilizers, unless the pharmacology mechanisms are not clear yet. Recent researchers reported common neuroprotective effects of mood stabilizers, suggesting a role of brain cell dysfunction in bipolar disorder and the dysfunction may eventually cause neuron loss. Volumetric neuroimaging, now increasingly assessing potential involvement of different brain structures in mood regulation, could be applied to test neuroanatomical models of mood disorders. Imaging studies suggested that ongoing neuronal atrophy accompanies bipolar disorder. For instance, PET images of the cerebral blood flow and the rate of glucose metabolism regarding as brain activity detected the reduced activity in subgenual prefrontal cortex during bipolar depression. This decrement in activity was, in part, at least explained by a corresponding reduction of cortical volume, as same as magnetic resonance imaging demonstration of the mean grey matter volume. In bipolar disorder, abnormalities of the third ventricle, frontal lobe, cerebellum, and possibly the temporal lobe are also noted.

Furthermore, studies had shown the significantly higher interleukin-6, interleukin-8 and TNF-α levels in bipolar patients during manic and depressive episodes than normal controls (Kim, H. W., Rim, H. D., Kim, J. H., Lee, S. J. Alexithymia and Stress Response Patterns among Patients with Depressive Disorders in Korea. *Psychiatry Investig.* 2009; 6(1): 13-8; O'Brien, S. M., Scully, P., Scott, L. V., Dinan, T. G. Cytokine profiles in bipolar affective disorder: focus on acutely ill patients. *J Affect Disord.* 2006: 90(2-3): 263-7; Brietzke, E., Stertz, L., Fernandes, B. S., Kauer-Sant'anna, M., Mascarenhas, M., Escosteguy Vargas, A., Chies, J. A., Kapczinski, F. Comparison of cytokine levels in depressed, manic and euthymic patients with bipolar disorder. *J Affect Disord.* 2009; 116(3): 214-7). In postmortem frontal cortex from bipolar disorder patients, the significantly higher protein and mRNA levels of IL-1β receptor and neuroinflammatory markers inducible nitric oxide synthase (iNOS) and c-fos were found (Rao, J. S., Harry, G. J., Rapoport, S. I., Kim, H. W. Increased excitotoxicity and neuroinflammatory markers in postmortem frontal cortex from bipolar disorder patients. *Mol. Psychiatry.* 2010; 15(4): 384-92). Taken together, the unbalance of immune system and subsequently leading to the neuronal inflammatory might related to the progression of the brain atrophy and aggravated the symptom of bipolar disorder.

Study had shown that treatment with immune-targeted therapies shown antidepressant properties. For example, open-label acetylsalicylic acid when added to fluoxetine led to increased remission rates in individuals with major depression whom were previously non-responsive to fluoxetine monotherapy (Mendlewicz, J., Kriwin, P., Oswald, P., Souery, D., Alboni, S., Brunello, N. Shortened onset of action of antidepressants in major depression using acetylsalicylic acid augmentation: a pilot open-label study. *Int Clin Psychopharmacol.* 2006; 21(4): 227-31). Thus, using the anti-inflammatory agent combine with the mood stabilizer might as a potential strategy to improve the treatment effect of bipolar disorder.

Recently, mood stabilizers have been shown to activate interconnected intracellular signaling pathways that promote neurogenesis and synaptic plasticity. Remarkable progress, at present, has been made in our understanding of the actions of mood stabilizers on neuron intracellular signaling pathways.

While the underlying therapeutic mechanisms are unclear, a growing body of evidence suggests that valproate (VPA) has neuroprotective and neurotrophic actions. Remarkably, the reduction in brain volume on bipolar patients was found to be largely suppressed by chronic treatment with VPA. An increasing number of reports show that long-term administration of VPA results in neuroprotective effects. It renders neurons less susceptible to a variety of insults (Chen P S, Peng G S, Li G, et al. Valproate protects dopaminergic neurons in midbrain neuron/glia cultures by stimulating the release of neurotrophic factors from astrocytes. Mol Psychiatry. December 2006; 11(12):1116-1125) and even stimulates neurogenesis in the adult rodent brain. VPA induces cytoprotective proteins like Bcl-2, glucose-regulated protein 78 (Grp78), brain-derived neurotrophic factor (BDNF) and heat shock protein 70. Moreover, VPA promotes neurite outgrowth, while VPA at therapeutic levels were reported to inhibit histone deacetylase (HDAC), an enzyme that catalyzes the removal of acetyl group from lysine residues of histones. Thus, the capability of VPA to covalently modify histone structures through enhanced acetylation may trigger changes in the expression of distinct downstream genes.

SUMMARY OF THE INVENTION

Figure 1:
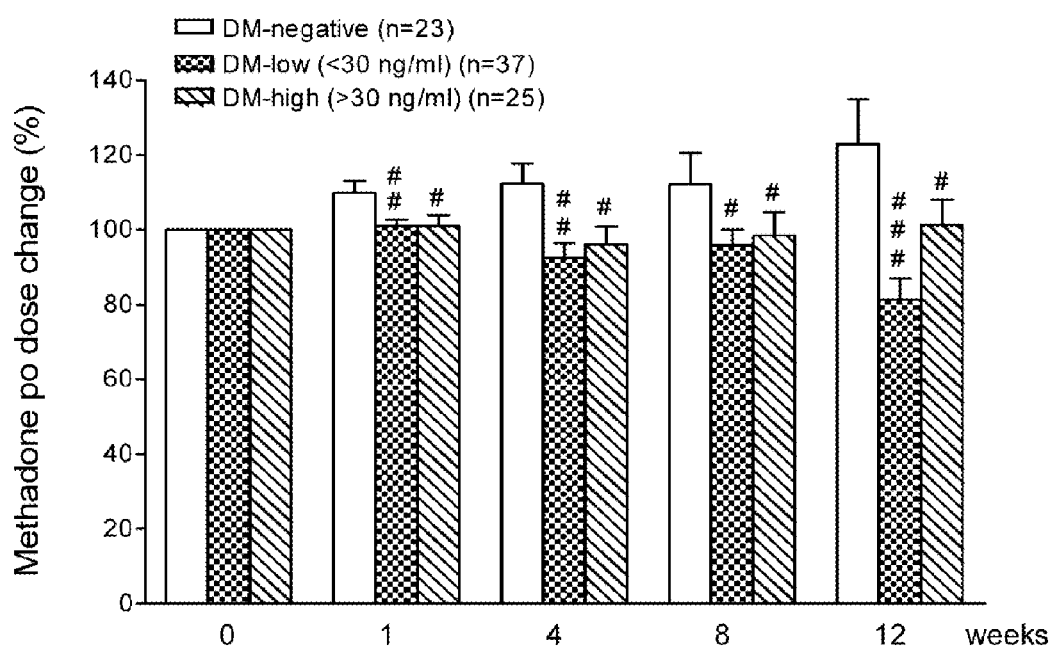
FIG. 1 shows methadone dosage change. effect is most significant at week 12, but can also be observed at weeks 1, 4, and 8. # P<0.05, # # p<0.01, # # # p<0.001 when compare to DM-negative group at the same week.

The present invention relates to a new use of Dextromethorphan in treating addictive behavior or bipolar disorder.

DETAILED DESCRIPTION OF THE INVENTION

The anti-inflammatory and neuroprotective effects of Dextromethorphan (DM) are the basis for the hypothesis that DM in combination with methadone can be used for the treatment for addictive behaviors.

The purposes of the present invention are to examine whether dextromethorphan is able to 1) reduce opioid tolerance and decrease methadone use; 2) reduce withdrawal symptoms; 3) decrease the relapse rate of opioid use, and 4) be an effective treatment for opioid dependence (and addictive behaviors).

In the present invention, the Applicant used 60 or 120 mg DM combined methadone maintain therapy in patients with opioid dependence.

The original purpose of methadone maintain therapy is to improve the quality of life in patients and decrease criminal rate. Therefore, not only will the present invention attempt to lower the drop-out rate of methadone use, but it also will promote the improvement of the quality of life as well as social security. However, the methadone also belongs to opioid compound and most of subject also combined heroin use in Taiwan.

In the long run, the present invention should lead to gaining a better understanding of the psychopharmacology on opioid dependence, which will be of great importance in developing appropriate treatments and/or preventative therapies. Moreover, the study design and the methodology of the present invention will be used to examine and understand other additional behaviors and psychiatric disorders.

Therefore, the present invention provides a method for treating addictive behavior, comprising administering Dextromethorphan (DM) to a subject suffering addictive behavior. In a preferred embodiment, the method can reduce opioid tolerance, decrease methadone use, reduce withdrawal symptoms or decreases relapse rate of opioid use. Preferably, the subject is human.

Base on knowledge gleaned from clinical and psychopharmacological studies, the combined treatment of mood stabilizers and DM is postulated to augment and improve the remedy for bipolar disorders. Thus, the other objective of the present invention is to determine whether combining the treatment of mood stabilizers and dextromethorphan produces the effects in improving the therapeutic efficacy for bipolar disorder patients.

In the present invention, it is found that the dextromethorphan add-on depakine treatment show more effective in hypomania stage in BP II patients after their receiving treatment for 8 weeks. Borderline improvement using CGI in BP I was further found. As well as the TNF-α, IL-1β, and IL-8 cytokines were also found to decrease after the add-on DM treatment. This result indicated that Dextromethorphan enhanced the Therapeutic Efficacy of Mood Stabilizes (depakine) in Bipolar Disorder Patients.

Moreover, it is found that both in opioid dependence and bipolar disorder patients, the anti-inflammatory drugs showed effects. In addition, it is noted that 30-40% of bipolar disorder patients combined with opioid dependence. Therefore, both disorders have relative pathogenesis was suggested.

Therefore, the present invention also provides a method for treating bipolar disorder, comprising administering Dextromethorphan (DM) to a subject suffering bipolar disorder. In a preferred embodiment, the bipolar disorder is bipolar I (BP-I) or bipolar II (BP-II). Dextromethorphan decreases plasma level of TNF-α or IL-8 in the subject. Preferably, the subject is human.

EXAMPLES

The examples below are non-limiting and are merely representative of various aspects and features of the present invention.

Example 1

Dextromethorphan (DM) for Treating Addictive Behavior

A. Research Designs and Methods

This was a double-blinded clinical research trial, randomly stratified, parallel groups, and single-centre study. A total of 85 male and female subjects with opioid dependency were recruited from methadone maintain therapy clinical. The proposal was sent to the Institutional Review Board of National Cheng Kung University for approval in order to maintain the protection of human subjects. Signed informed consent was obtained from each subject before inclusion. Eligible subjects were Han Chinese living in Taiwan, and were psychiatric out- and in-patients who sought for psychiatric care or had been referred for psychiatric evaluation with clinically suspected opioid dependency between 18 and 65 years of age. They had to be able to communicate with either Mandarin or Taiwanese.

Patient Resource

Subjects with opioid dependence were recruited from the list of current opioid users and were restricted on methadone treatment as the opioid using group. In the opioid using group, DM add-on or placebo treatment in a double-blind fashion was conducted for 12 weeks after completion of structured diagnostic interviews and treatment with methadone in the optimal dose range. Urine tests were examined weekly for opioid use.

Instruments, Assessment Scales and Neuropsychological Testing

Chinese Version of the Mini International Neuropsychiatric Interview (MINI)

The MINI was the most widely used psychiatric structured diagnostic interview instrument in the world, and it was a brief interview tool developed in France and the United States to screen for major axis I psychiatric disorders listed in the Diagnostic and Statistical Manual of Mental Disorders (4th ed.; DSM-IV) and International Classification of Diseases (10th ed.; ICD-10). Studies of validation and reliability comparing the MINI to the Structured Clinical Interview for DSM-III-R-Patient version (SCID-P) and the Composite International Diagnostic Interview (CIDI) showed that the MINI had an acceptably high validation and reliability score, and could be administered in a shorter period of time than other referenced instruments. The Taiwan Chinese version of the MINI had been translated by Lee et al. and had good reliability (unpubl. data). The instrument was fully structured to allow administration by non-specialized interviewers. Subjects were interviewed by psychiatric specialists using the MINI (Sheehan et al., 1998; Taiwanese Society of Psychiatry, 2001).

Patient Selection

This clinical trial could only fulfill its objectives if appropriate subjects were enrolled. The following eligibility criteria were designed to select patients for whom protocol treatment was considered appropriate. All relevant medical and non-medical conditions should be taken into consideration when deciding whether this protocol was suitable for a particular patient. All subjects were interviewed with MINI by a trained specialist to confirm the diagnosis and to evaluate the co-morbidity. Eligibility criteria might not be disregarded by the investigator and were subjected to review in the case of a Good Clinical Practices (GCP) or a regulatory authority audit.

1. Inclusion Criteria

Patients who met all of these inclusion criteria were eligible for enrollment into the study:
(1) Signed informed consent by patient or legal representative.
(2) Male or female patient aged ≥18 and ≤65 years.
(3) A diagnosis of opioid dependence according to DSM-IV criteria made by a specialist in psychiatry.

(4) Patient or a reliable caregiver could be expected to ensure acceptable compliance and visit attendance for the duration of the study.

2. Exclusion Criteria

The presence of any of the following would exclude a patient from study enrollment:
 (1) Women of childbearing potential, not using adequate contraception as per investigator judgment or not willing to comply with contraception for the duration of the study.
 (2) Females who were pregnant or nursing.
 (3) Patient had received DM or other anti-inflammatory medications within 1 week prior to the first dose of the double-blinded medication.
 (4) Other major Axis-I DSM-IV diagnosis other than opioid dependence and diagnosis as multiple substance dependence within 1 year prior to the first dose of the double-blinded medication.
 (5) Current evidence of an uncontrolled and/or clinically significant medical condition, e.g., cardiac, hepatic and renal failure that would compromise patient safety or preclude study participation.
 (6) History of intolerance to methadone or DM.
 (7) History of sensitivity reaction (e.g., urticaria, angioedema, bronchospasm, severe rhinitis, anaphylactic shock) to DM.
 (8) Patient had received electroconvulsive therapy (ECT) within 4 weeks prior to the first dose of the double-blinded medication.
 (9) Increase in total SGOT, SGPT, gamma-GT, BUN and creatinine by more than 3×ULN (upper limit of normal).

Procedures

The add-on double-blinded study treatment with DM was commenced at randomization for 12 weeks. Subjects were grouped into the opioid using group and visited methadone maintenance clinics in order to take the necessary methadone dosage. Accordingly, the dose of methadone was adjusted in correspondence to the patient's clinical situation. If a patient was intolerable to increasing doses of methadone, they would have the dose reduced by 5 mg as necessary. Patients were randomized at Baseline to commence the double-blinded add-on treatment of either DM (60 mg, 120 mg/day in sustained-release dosage form) or placebo two times a day. The dosage of methadone was increased or decreased a maximal 5 mg each time. The dose of methadone was recorded at every visit.

Concomitant benzodiazepine medication (preferably up to 16 mg lorazepam) might be used for nighttime sedation, agitation or insomnia during the study. All subjects were evaluated weekly in the initial month and biweekly after the second month.

Blood Sample Assessment

Blood routine (RBC, WBC, Hb, Hct, MCV, MCH, MCHC, PLT, Lymph), SGOT, SGPT, BUN and creatinine were measured only in the samples taken at Screen and at the end of the study.

Immunological Markers Assessment

1. Measurement of Cytokine and Chemokine Profiles for Human Studies

Human Cytokine Array I (Ray Biotech Inc., Norcross, Ga.) consisted of 23 different cytokine and chemokine antibodies spotted in duplicate onto a membrane (Dvorakova et al. 2004). The membranes were blocked with 10% bovine serum albumin in Tris-buffered saline according to the instructions of the manufacturer. One and a half milliliters of conditioned medium was added to each membrane in separate wells of a six-well plate. The membranes were shaken at 110 rpm at room temperature for an hour and a half. All washes were done in new six-well plates, according to the instructions of the manufacturer. Two milliliters of a 1:500 dilution of biotinconjugated antibodies was added to each membrane, and the mixture was incubated on a shaker for an hour and a half at room temperature. Following the wash, the membranes were incubated with a 1:40,000 dilution of strepavidin-conjugated peroxidase for 1 hour at room temperature, according to the instructions of the manufacturer. Following a thorough wash, the membranes were exposed to a peroxidase substrate (Chem-Glow West; Alphalnnotech Corp., San Leandro, Calif.) for 5 min in the dark before imaging. Two or six individual membranes were placed side-by-side in a plastic protective folder and sealed. Imaging was done with a UVP AutoChemi imaging system within 30 min of exposure to the substrate. Exposure times ranged from 1 to 10 min. Chemiluminescence was quantified with LabWorks imaging and analysis software. Horseradish peroxidase (HRP)-conjugated antibody served as a positive substrate control at six spots and was also used to identify membrane orientation. For each spot the net density gray level was determined by subtracting the background gray levels from the total raw density gray levels. The relative fold difference in cytokine amount was determined in reference to the amount present on the control culture membrane based on the following: average treated culture cytokine spot gray levels/average control culture cytokine spot gray levels.

2. ELISA

Cytokine was quantified by using the Flexia antibody pair system (Bio-Source Intl., Camarillo, Calif.). Basically, the enzyme-linked immunosorbent assays (ELISAs) were optimized by using 96-well plates (MaxiSorp; Nalge Nunc International Corp., Naperville, Ill.) coated with 100 µl of strepavidin (Sigma, St. Louis, Mo.) at 5 µg/ml in water overnight at 37° C. or until all water was evaporated. All plates were stored desiccated at 4° C. until use. Biotinylated F(ab)2 coating antibody (5 µg/ml) was added to each well, and the plate was incubated at 37° C. for 2 hours. All wells were blocked and washed according to the instructions of the manufacturer. Standards or samples (100 µl) were added to the wells, and the plates were incubated at 37° C. for 1 hour. HRP-conjugated antibody (10 µg/ml) was added for an additional hour at 37° C. The plates were then washed thoroughly according to the instructions of the manufacturer. One hundred microliters of tetramethlybenzidine substrate (Roche, Indianapolis, Ind.) was added to each well, and the plates were held for 30 min in the dark. The reaction was stopped by the addition of 100 µl of 2 $NH_2SO_4$ to each well. The absorbance was read on an automated plate reader (Tecan U.S. Inc.) at 450 nm (reference wavelength, 650 nm). Values (in picograms per milliliter) were calculated from a standard curve. Samples were diluted up to 1:20, depending on the concentration.

The immunological parameters, C-reactive protein, TNF-α and interleukins was measured in the blood samples taken at Screen, week 1, week 4, week 8 and at the end of the study.

Plasma Level Assessment

HPLC with UV detector was used to measure the plasma dextromethorphan and methadone level.

Urinary Assessment

Urinary opioid examinations was measured nonscheduled and at every visit.

The dose of methadone was recorded at every visit.

Statistical Methods

The demographic and clinical characteristics of the patients, the dextromethorphan/methadone doses, and the adverse effects were compared among groups by using Kruskal-Wallis tests for continuous variables and $\chi^2$ tests for categorical variables. To assess the efficacy in various clinical domains and to take into account patient effects, mixed-effects models (Lange & Ryan 1989) were used (with intercept as the random effects) for all normally distributed outcomes, with main effects for treatment (DM or placebo), time (0, 1, 2, 4, 8, 12 weeks), and the treatment×time interaction. The significance of treatment effects across time was assessed by the significance of the treatment×time interaction while controlling for the main effects. Unlike the analysis of variance, the mixed-effects model did not need to set a statistical p value in all groups. Multiple linear regressions could be applied only if the distribution of the response values was symmetrical. For outcome variables with non-normal distributions, Mann-Whitney tests between pairs of treatments were used. Significance was assessed by comparing endpoint data while controlling for baseline data. The estimated odds of marked treatment response during the study were analyzed based on multiple logistic regressions. However, because no mixed-effects model was available for multiple logistic regressions, the generalized estimating equation (Zeger, S. L., Qaqish, B. Markov regression models for time series: a quasi-likelihood approach. *Biometrics*. 1988; 4(44): 1019-31) method (for fixed-effects models) was used herein. For repeated-measures studies (such as the present one), longitudinal follow-up data obtained from the same patient, however, were intra-individually related and violated the "independent" requirement of multiple linear regression. To adjust this within-subject dependence effect, Zeger et al. (1988) proposed a generalized estimating equation statistical method for generalized linear models in repeated-measures studies. In the present invention, the odds ratio of responder status was modeled to compare the placebo and dextromethorphan groups. The analysis of the response rate was intent to treat. All hypothesis tests were 2-sided and were conducted at $\alpha=0.05$.

Demographic and clinical variables, age and education years were analyzed in the ANOVA model with diagnostic effects. Categorical variables such as gender were compared using $\chi^2$ test.

For each scale, data were analyzed using a last observation carried forward (LOCF) method, in which the last observation was entered for missing visits, and an observed-case (OC) method. Dichotomous data including gender and percentages of patients who discontinued treatment were compared between the treatments using $\chi^2$ test. Other baseline clinical characteristics including intergroup baseline scores, age, weight and height were analyzed using Student's t-test. A general linear model for analysis of covariance (ANCOVA) with the factor for treatment and with baseline total score as a covariate was used to analyze the primary outcome, the mean change from baseline to week 12 in the total score at each schedule after baseline visit. Differences in response and remission rates were calculated on an LOCF basis at each scheduled visit using Fisher's exact test.

$P<0.05$ was considered statistically significant for all two-sided tests. Statistical analyses were carried out using SPSS for windows.

B. Human Subjects

1. Subject population. Subjects with opioid use were collected. Men and women of ages ranging from 18 to 65 were eligible for the study if they met DSM-IV (American Psychiatric Association 1994) criteria for opioid dependence in the past or at the present, and all of them were free of a history of other major mental illnesses, including multiple substance dependence.

2. Potential risks. There were minimal risks associated with drawing blood from adults for either blood sample routine testing or for establishing immunological markers. However, in the case where subjects might become uncomfortable during the blood drawing, an attending physician was present. Subjects were free to withdraw from the study at any time.

Figure 2:
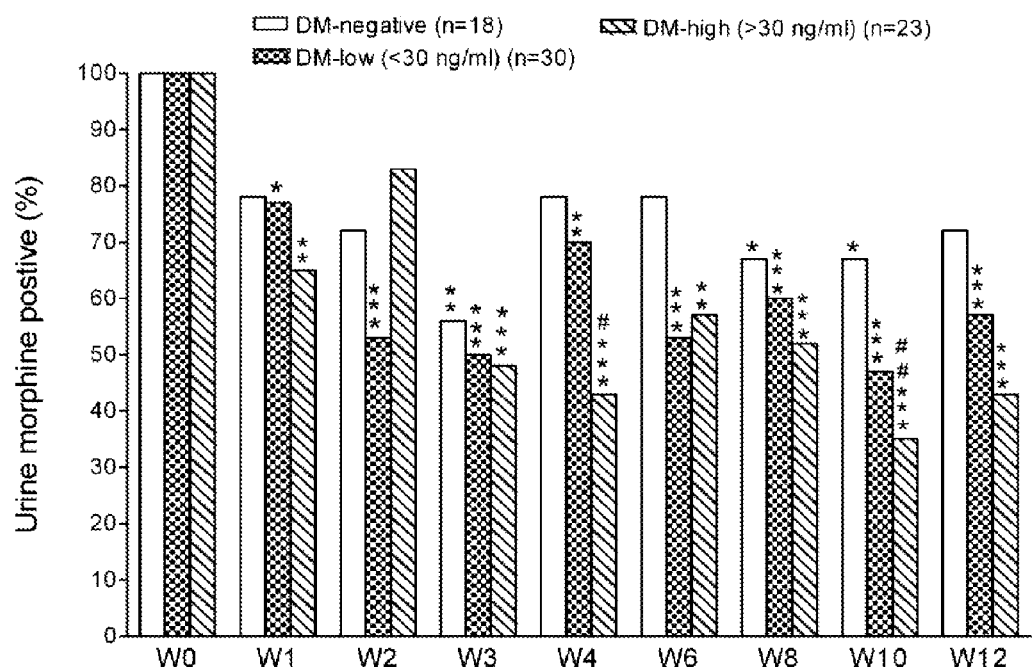
FIG. 2 shows urine morphine positive finding. * P<0.05, * * p<0.01, * * * p<0.001 when compare to the WO at the same group. # P<0.05, # # p<0.01 represent the significant difference when compare to the DM-negative group at the same week.
Figure 3:
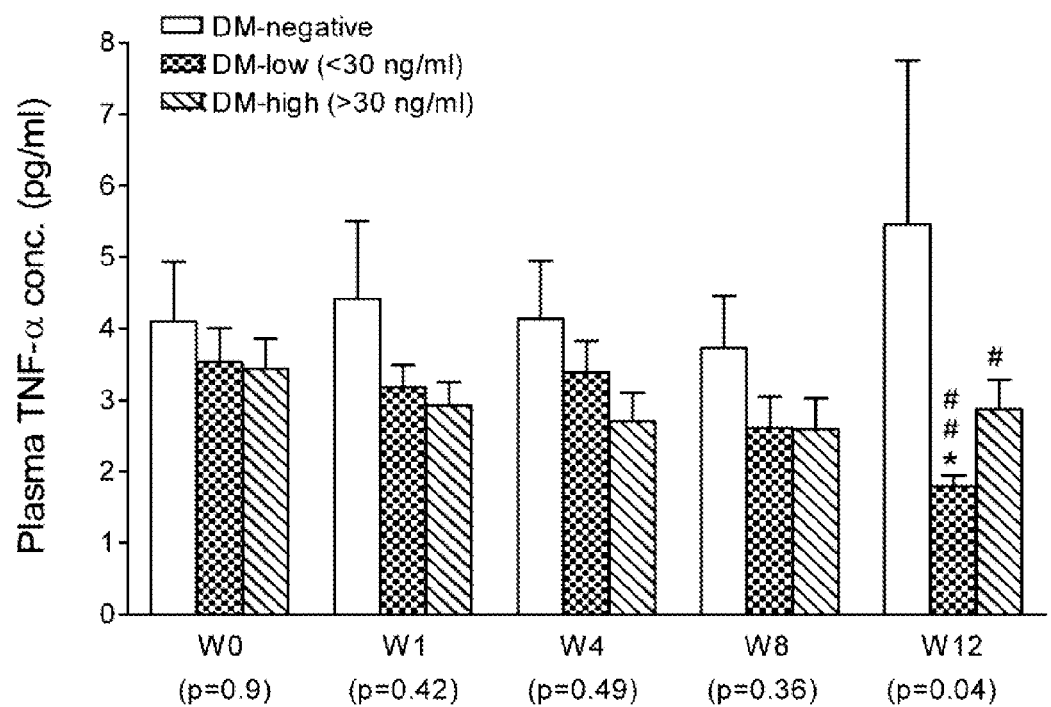
FIG. 3 shows plasma TNF-alpha concentration. * P<0.05 represents the significant difference when compare to the WO at the same group (One-way ANOVA). # P<0.05, # # p<0.01 represent the significant difference when compare to DM-negative group at the same week.
Figure 4:
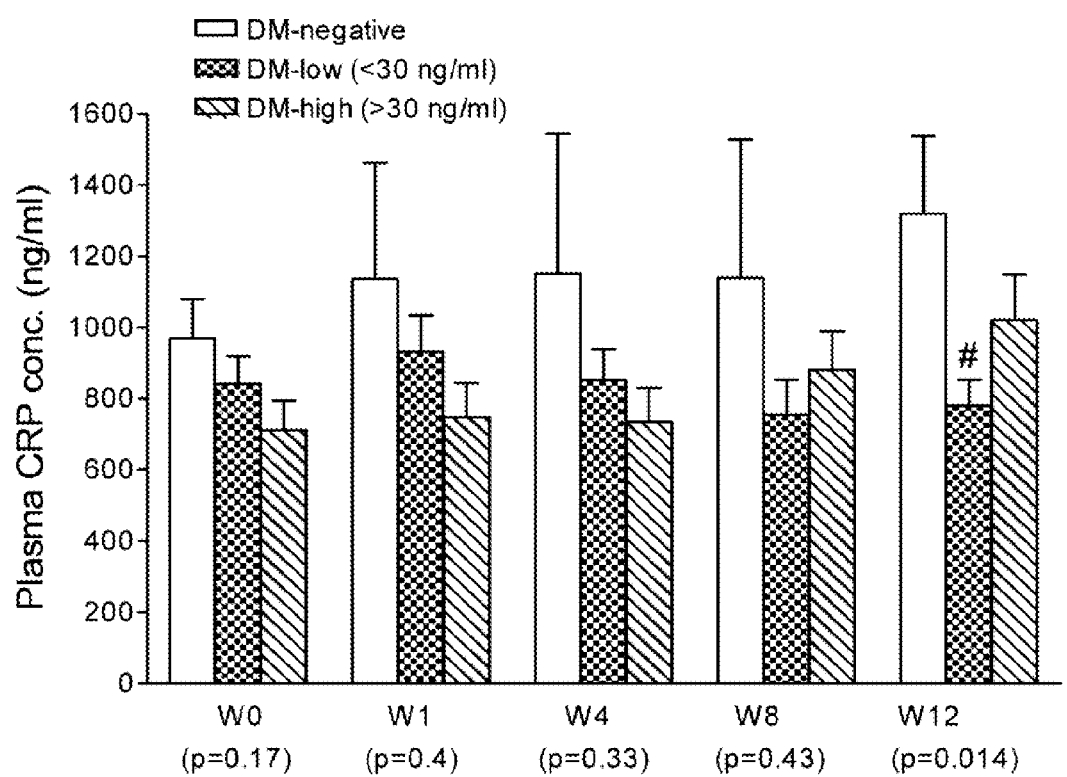
FIG. 4 shows plasma CRP concentration. # P<0.05 represents the significant difference when compare to DM-negative group at the same week (One-way ANOVA).
Figure 5:
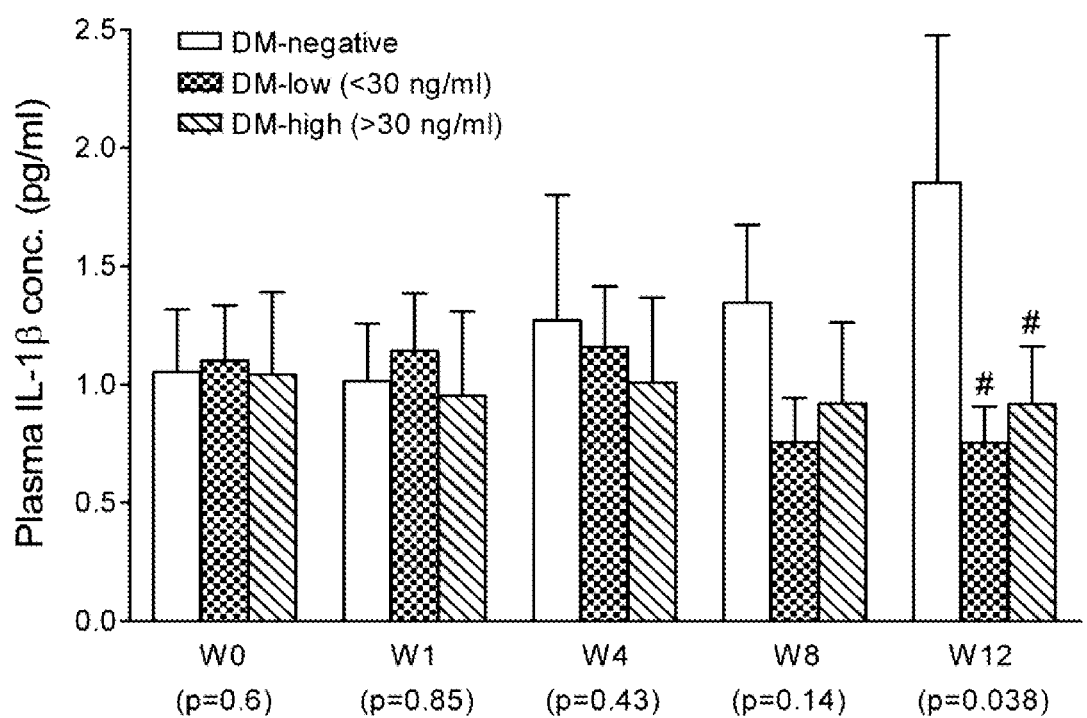
FIG. 5 shows plasma IL-1 beta concentration. # P<0.05 represents the significant difference when compare to DM-negative group at the same week (One-way ANOVA).
Figure 6:
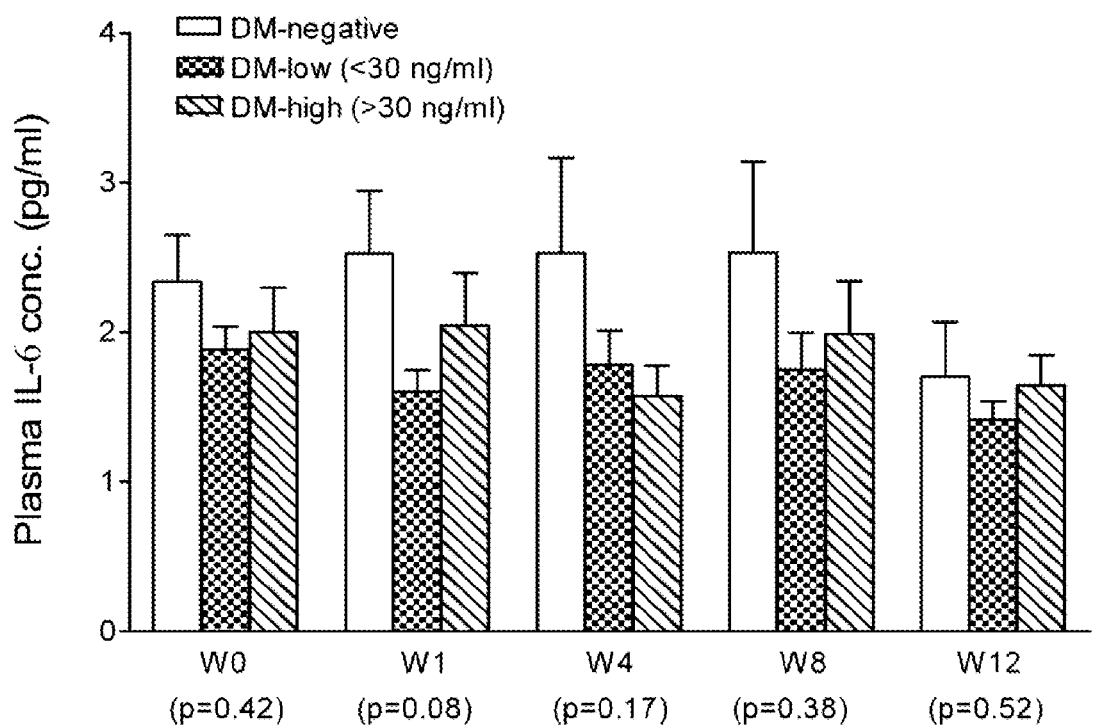
FIG. 6 shows plasma IL-6 concentration.
Figure 7:
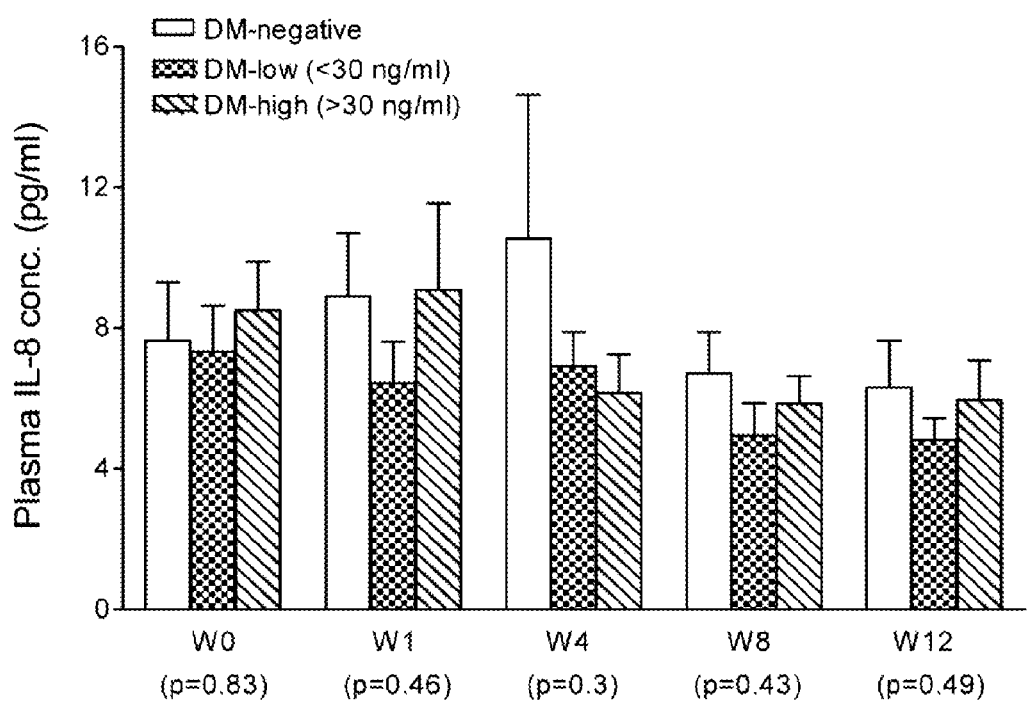
FIG. 7 shows plasma IL-8 concentration.
Figure 8:
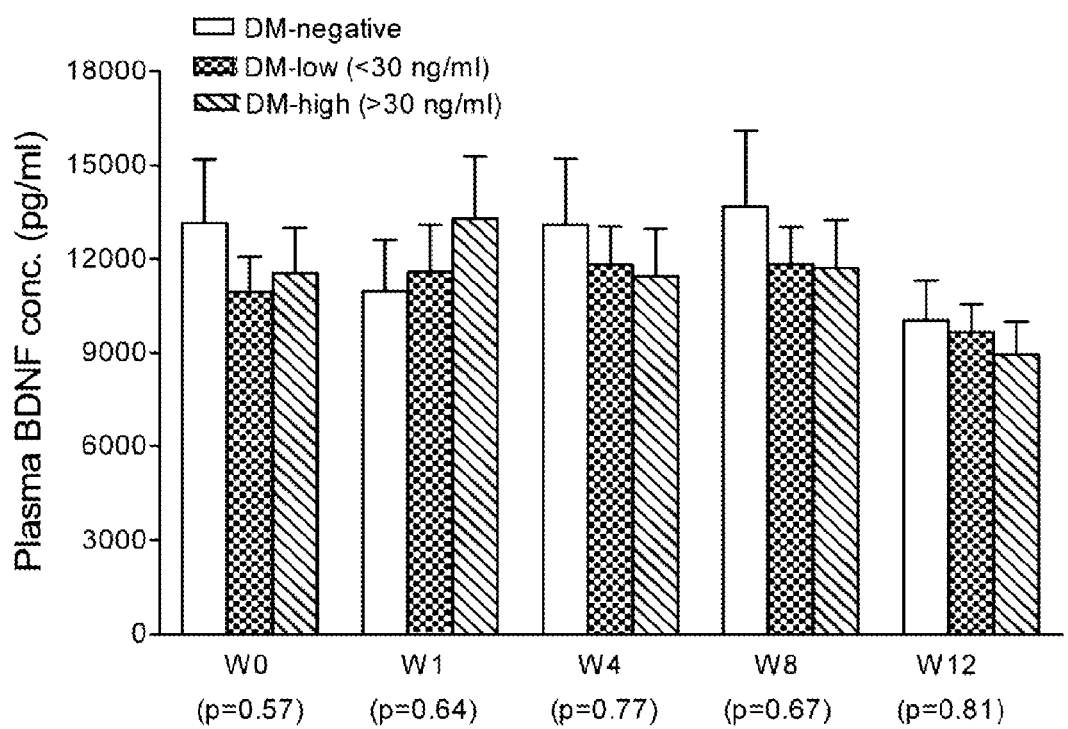
FIG. 8 shows plasma BDNF concentration.

Results:

Totally 120 subjects were recruited, 35 participants dropped out. The dropout rate was 29%. The remaining 85 participants were divided into three groups according to plasma concentration of DM: twenty-three subjects of placebo, 25 subjects of the high plasma dextromethorphan level (>30 ng/ml) and 37 subjects of the low plasma dextromethorphan level (<=30 ng/ml). The results showed that low dose DM group showed the highest tendency of decrease of methadone use compared with that of the high-dose DM group and the placebo group (FIG. 1). Both high and low plasma dextromethaphan level groups had lower percentage morphine-positive urine compared to that of the placebo group (FIG. 2). Significantly lower plasma TNF-alpha concentration were observed in both high or low plasma DM groups compared with that of the placebo group, but the low plasma DM group showed a tendency of more decrease of plasma TNF-alpha concentration (FIG. 3). The lower plasma CRP concentration was found only in low plasma DM group (FIG. 4). The lower plasma IL-1beta concentration was noted both in high or low plasma dextromethorphan level groups compared to that of the placebo group (FIG. 5). There were no significant differences between groups throughout the 12-week treatment in IL-6, IL-8 and BDNF (FIGS. 6, 7 & 8).

Example 2

Dextromethorphan (DM) for Treating Bipolar Disorder Method

Patent Selection

Totally 292 male and female subjects with bipolar I or II disorder, from the Department of Psychiatry at National Cheng Kung University Hospital and National Defense Medical Center were recruited. Eligible subjects were psychiatric out- and in-patients who sought psychiatric care or had been referred for psychiatric evaluation with clinically suspected of having mood disorder, between 18 and 65 years of age and could understand Chinese or Taiwanese. The Institutional Review Board for the Protection of Human Subjects approved the study protocol by both medical centers. Signed informed consent was obtained from each subject before inclusion.

The inclusion criteria were as follows: 1) Bipolar I or II disorder according to DSM-IV criteria; 2) A total of HDRS scored at least 18 or YMRS scored at least 14 at the screening stage; 3) Male or female patient aged ≥18 and ≤65 years; 4) Signed informed consent by patient or legal representative; 5) Patient or a reliable caregiver were expected to ensure acceptable compliance and visit attendance for the duration of the study.

The presence of any of the following excluded a patient from the study enrollment: 1) Females who were pregnant or nursing; 2) Women of childbearing potential not using adequate contraception as per investigator judgment or not willing to comply with contraception for duration of study; 3) Patient had received dextromethorphan, or other selective cyclo-oxygenase 2 (Cox-2) inhibitors, or other anti-inflammatory medication within 1 week prior to first dose of double-blind medication; 4) Major mental illness including alcoholism and illegal substance use disorder; 5) Clinically significant medical condition; 6) Current evidence of an uncontrolled and/or (e.g., cardiac, hepatic and renal failure); 7) Patient had received electroconvulsive therapy (ECT) within 4 weeks prior to the first dose of double-blind medication; 8) Increased in total SGOT, SGPT, BUN and creatinine by more than 3×ULN (upper limit of normal).

Study Design

The add-on double-blind study treatment with DM/place was commenced at randomization for 12 weeks while patients continue open-label VPA. Subjects were randomized to either with 60 mg per day of DM or placebo at Baseline and proceeded to double-blind Add-On Treatment. The treatment response and side effect were measured to clarify the curative effect of DM add-on therapy to VPA in the treatment of bipolar disorders. Patients had an open-label pre-randomization Valproate-only Treatment period where VPA was dosed between 500 mg and 1000 mg daily (50-100 µg/ml in plasma). Concomitant benzodiazepine medication (preferably up to 8 mg lorazepam) was used for daytime sedation, agitation or insomnia during the study. Risperidone 1-6 mg/daily and fluoxetine 20 mg/daily were permitted during manic or depressive stage, and anticholinergic drug was also used for the extrapyramidal syndrome (EPS).

Main Outcome Measures

The Chinese version of the modified SADS-L, a semi-structured interview aimed at formulating the main diagnoses based upon DSM-IV criteria with good inter-rater reliability. This modified version of SADS-L with its diagnoses was used as the gold standard. The severity of current symptoms was assessed by using the YMRS and HDRS. The diagnoses of a mood disorder were made according to DSM-IV criteria, except for bipolar II disorder, where the duration criterion for hypomania of 4 days was left out but 2-day cutoff for hypomania was used instead, because the 4 days minimum duration might not be based on data and the newly adopted cutoff had been supported by several previous reports. The side effect was measured using Clinical Global Impression (CGI) at each visit point.

Blood Sample Assessment and Plasma Cytokine Level

Blood routine, SGOT, SGPT, BUN and creatinine were measured only while the samples were taken at screen and at the end of the study. Plasma cytokine was quantified using the enzyme-linked immunosorbent assays (ELISAs). The Quantikine Human cytokine kit (R&D system), and Molecular Devices (SpectraMax-M2) ELISA reader were used to analyze the plasma cytokine level. The immunological parameters, BDNF, TNF-α, and interleukins were measured in the blood samples. The low limit sensitivity was 0.5 pg/ml, 0.125 pg/ml and 62.5 pg/ml for TNF-α, IL-1β and BDNF respectively. Finally, we used HPLC with UV detector to measure the plasma DM level.

All of the above, vital sign, and immunological markers were measured at baseline, 1, 2, 4, 8 and 12 weeks. For the 30 subjects of health control were also recruited for comparing the immune markers. The degree of benefit on symptoms after the week 4, 8 and end of treatment due to add-on DM treatment to VPA in comparison with placebo using a main measure of total psychopathology. The safety and tolerability and measure and assess the changes of immunology, and clinical features between the group with add-on DM treatment with placebo from Baseline to the end of study were compared.

Statistical Analyses

The demographic and clinical characteristics of the patients were compared among groups by using $\chi^2$ tests for categorical variables.

For each scale, data were analyzed using last observation carried forward (LOCF) method, in which the last observation was entered for missing visits. To assess the efficacy in various clinical domains and take into account patient effects, mixed-effects models (Lange & Ryan 1989) were used (with intercept as the random effects) for all normally distributed outcomes, with main effects for treatment (DM or placebo), time (0, 1, 2, 4, 8, 12 weeks), and the treatment×time interaction. The analysis of the response rate was intent to treat. All hypothesis tests were 2-sided and were conducted at $\alpha=0.05$. The post hoc of independent t test was then used to examine which time point the effect of add-on treatment started. $P<0.05$ was considered statistically significant for all two-sided tests. Statistical analyses were carried out using SPSS for windows (version 15.0).

Results:

Patients 292 subjects were collected including Bipolar I: 136, Bipolar II: 156. Ninety-four BP I and 81 BP II had completed the 12 week-treatment course (the drop-out rate was 30.8% and 48% respectively). The Plasma dextromethorphan levels were measured by HPLC showing that 84 BP I and 82 BP II patients had regular drug compliance at least for the first 4 weeks. There were no differences of the demographic data between the analyzed group and drop-out group (Table 1).

TABLE 1

The demographic data of BP patients in the analyzed and drop-out groups

| Group | BPI | | | BPII | | |
|---|---|---|---|---|---|---|
| | Analyzed (n = 84) | Drop-out (n = 52) | t/X² (p-value) | Analyzed (n = 82) | Drop-out (n = 74) | t/X² (p-value) |
| Age | 34.10 ± 12.14 | 31.40 ± 10.39 | −1.33 (0.19) | 29.20 ± 9.83 | 30.95 ± 12.10 | 1.00 (0.32) |
| Gender (Male/Female) | (39/45) | (29/23) | 1.12 (0.29) | 45/37 | 37/37 | 0.37 (0.54) |

Efficacy

Figure 9:
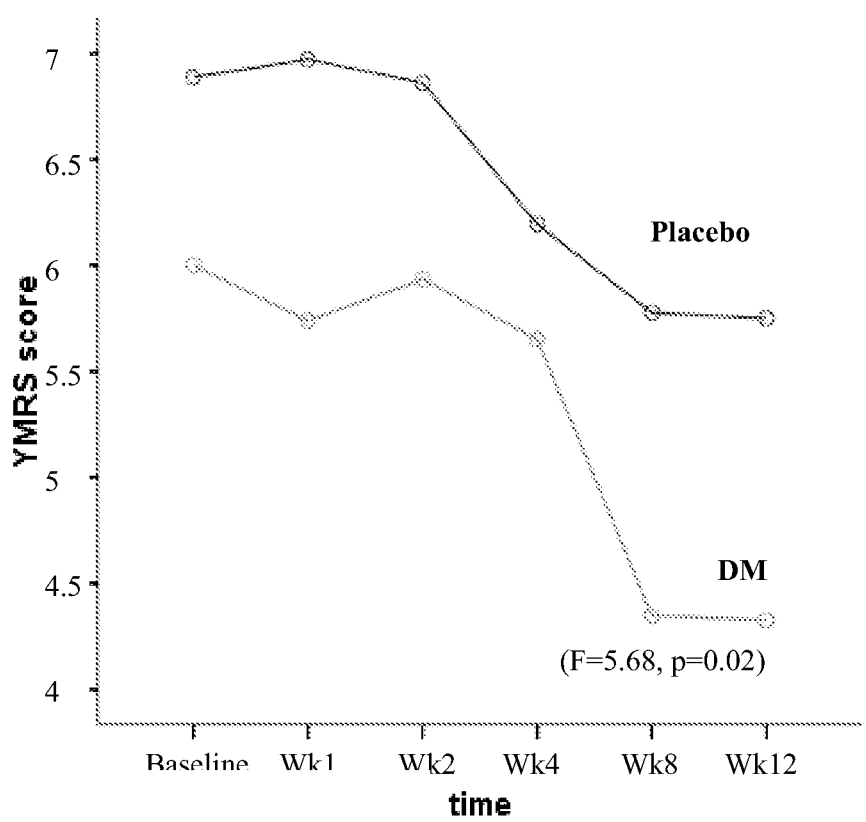
FIG. 9 shows the change of YMRS score in BP II subjects.

The data analyzed group was divided into: DM group 49, placebo group 35 in BP I, and DM group 46, placebo group 36 in BP II. One hundred and ninety six subjects' immunological markers had assessed, including 166 subjects of BP and 30 normal controls. A significant difference of YMRS score between two groups in BP II (F=5.68, p=0.02) was found. In addition, the post hoc t test showed significant differences between groups were at the week 8 (p=0.01) and 12 (p=0.008), but not HDRS (Table 2, FIG. 9).

TABLE 2

The Post hoc: t test in the two BP groups

| | BPI | | | BPII | | |
|---|---|---|---|---|---|---|
| time | Placebo | DM | t (p-value) | Placebo | DM | t (p-value) |
| Baseline | 8.23 ± 4.37 | 8.08 ± 5.35 | −0.25 (p = 0.81) | 6.89 ± 3.98 | 5.77 ± 3.25 | 1.38 (p = 0.17) |
| Week 1 | 7.46 ± 4.90 | 8.08 ± 5.35 | −0.55 (p = 0.59) | 6.97 ± 4.20 | 5.60 ± 2.99 | 1.69 (p = 0.10) |
| Week 2 | 7.31 ± 5.00 | 7.31 ± 5.00 | −1.78 (p = 0.08) | 6.86 ± 3.50 | 5.88 ± 3.13 | 1.31 (p = 0.19) |
| Week 4 | 7.00 ± 4.97 | 5.86 ± 3.01 | 1.21 (p = 0.23) | 6.19 ± 2.69 | 5.60 ± 2.90 | 0.93 (p = 0.36) |
| Week 8 | 6.37 ± 3.93 | 6.16 ± 3.61 | 0.25 (p = 0.80) | 5.78 ± 2.60 | 4.40 ± 2.26 | 2.53 (p = 0.01) |
| Week 12 | 5.06 ± 3.43 | 5.80 ± 4.04 | −0.88 (p = 0.38) | 5.75 ± 2.74 | 4.26 ± 1.97 | 2.74 (p = 0.008) |

Figure 10:
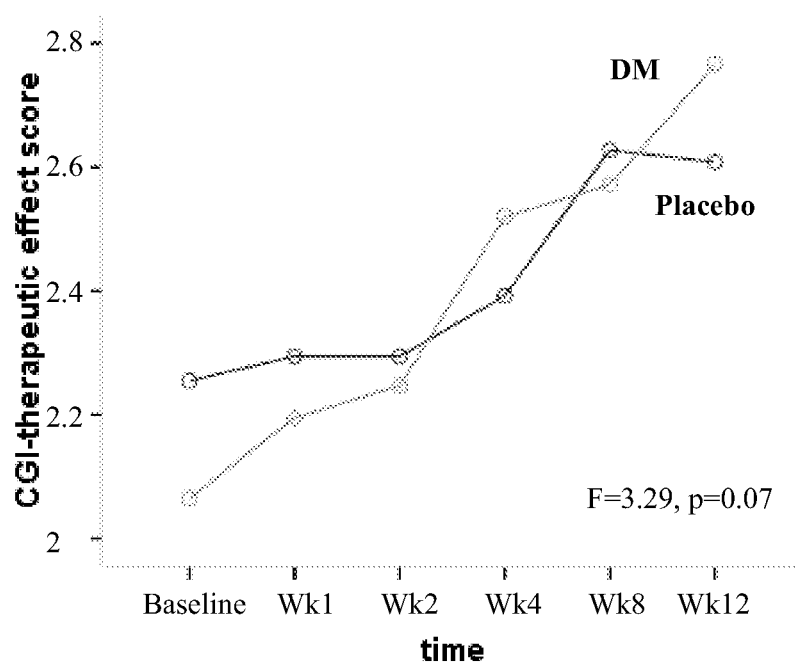
FIG. 10 shows the changes of CGI-therapeutic effect score by the time changes.
Figure 11:
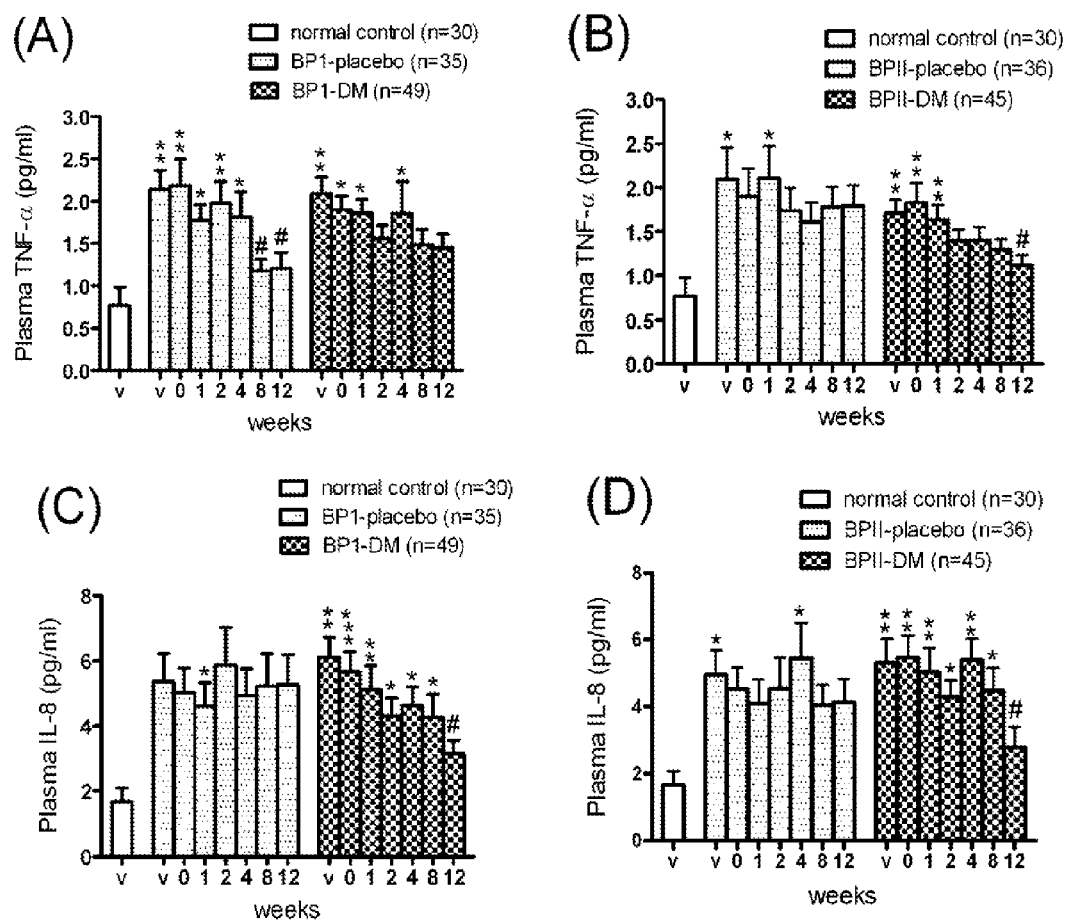
FIG. 11 shows plasma cytokine (TNF-α & IL-8) level before and after DM add on depakine treatment in BP subjects. * * * P<0.001, * * p<0.01, * p<0.05 vs. normal control (One-Way ANOVA); # p<0.05 vs. pretest data (v) within the same group (One-Way ANOVA).

A borderline significance of CGI-therapeutic effect score was found in BP I (p=0.07) (FIG. 10), but no differences of either YMRS or HDRS were found in BP I. In the plasma immune markers, it is found that for most of the TNF-α, IL-1β, and IL-8, BP subjects had higher levels than did the normal controls at the baseline (FIG. 11); after receiving 12 weeks treatment with depakine add-on dextromethorphan the significant decreasing plasma TNF-α and IL-8 level were found (FIG. 11). However, no difference of CRP and BDNF between normal controls and BP subjects was found before and after treatment (data not show).

One skilled in the art readily appreciates that the present invention is well adapted to carry out the objects and obtain the ends and advantages mentioned, as well as those inherent therein. The uses of drugs are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for treating addictive behavior, consisting of administrating Dextromethorphan (DM) to a subject suffering from addictive behavior, wherein the dose of Dextromethorphan (DM) is equal to or lower than 60 mg/day.

2. The method of claim 1, which reduces opioid tolerance.

3. The method of claim 1, which decreases methadone use.

4. The method of claim 1, which reduces withdrawal symptoms.

5. The method of claim 1, which decreases relapse rate of opioid use.

6. The method of claim 1, wherein the subject is human.

7. A method for treating bipolar disorder, comprising administrating Dextromethorphan (DM) to a subject suffering from bipolar disorder, wherein the dose of Dextromethorphan (DM) is equal to or lower than 60 mg/day.

8. The method of claim 7, wherein the bipolar disorder is bipolar I (BP-I) or bipolar II (BP-II).

9. The method of claim 7, which decreases plasma level of TNF-α or IL-8 in the subject.

10. The method of claim 7, wherein the subject is human.

11. The method of claim 1, which reduces opioid craving.

\* \* \* \* \*